United States Patent [19]

Bolhofer

[11] 3,953,465
[45] Apr. 27, 1976

[54] 2-[α-(3-TRIFLUOROMETHYLPHENOXYL)-4-CHLOROBENZYL]OXAZOLE AND METHODS FOR PREPARING THE SAME

[75] Inventor: William A. Bolhofer, Frederick, Pa.

[73] Assignee: Merck & Co., Inc., Rahway, N.J.

[22] Filed: Oct. 26, 1973

[21] Appl. No.: 410,130

Related U.S. Application Data

[62] Division of Ser. No. 243,480, April 11, 1972, Pat. No. 3,816,446.

[52] U.S. Cl............................................. 260/307 R
[51] Int. Cl.².................................... C07D 263/32
[58] Field of Search ................................ 260/307 R

[56] References Cited
UNITED STATES PATENTS 3,816,446   6/1974   Bolhofer ........................... 260/307

Primary Examiner—Raymond V. Rush
Attorney, Agent, or Firm—Richard A. Thompson; J. Jerome Behan

[57] ABSTRACT

[α-(3-Trifluoromethylphenoxy)-4-chlorobenzyl heterocycles which are prepared by the cyclization of an appropriately substituted [α(3-trifluoromethylphenoxy)-4-chlorobenzyl]compound. The products reduce the concentration of cholesterol, trigylcerides and other lipids in blood serum and are therefore useful in the treatment of atherosclerosis.

1 Claim, No Drawings

2-[α-(3-TRIFLUOROMETHYLPHENOXYL)-4-CHLOROBENZYL]OXAZOLE AND METHODS FOR PREPARING THE SAME

This application is a division of Ser. No. 243,480 filed Apr. 11, 1972 and now U.S. Pat. No. 3,816,446.

It is an object of this invention to describe a new class of chemical compounds which can be characterized as [α-(3-trifluoromethylphenoxy)-4-chlorobenzyl]-heterocycles.

Also, it is an object of this invention to describe a process for the preparation of the [α-(3-trifluoromethylphenoxy)-4-chlorobenzyl]heterocycles.

Clinical studies shown that cholesterol plays a major role in the formation of atherosclerotic plaques by accelerating the deposition of blood lipids in the arterial wall. It is the purpose of this invention to disclose a new class of chemical compounds which effectively reduce the concentration of cholesterol, triglycerides and other lipids in blood serum and are therefore useful in the treatment of atherosclerosis.

The products of this invention are compounds having the following general formula:

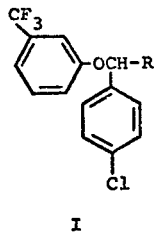

I wherein R is a heterocycle, for example, a 5-membered-heterocycle containing from 2–4 hetero atoms selected from oxygen and nitrogen such as tetrazolyl, oxazolyl, oxazolinyl and the like.

A preferred embodiment of this invention relates to 5-[α-(3-trifluoromethylphenoxy)-4-chlorobenzyl]tetrazole (Ic, infra). This compound exhibits a particularly good hypocholesterolemic and hypolipemic activity.

The products of this invention are prepared by treating the appropriate starting material with a reagent capable of producing a heterocycle substituent. In general, the reaction can be viewed as a cyclization of an appropriate starting material. The process comprises: (1) treating an N-(2-hydroxyethyl) (3-trifluoromethylphenoxy) (4-chlorophenyl)acetamide with a cyclizing agent; (2) treating an N-(β,β-dichloroethyl) (3-trifluoromethylphenoxy) (4-chlorophenyl)acetamide with a cyclizing agent; or (3) cyclizing 1-imino-1-azido-2-[(3-trifluoromethylphenoxy) (4-chlorophenyl)]ethane.

The process affords, respectively, 2-[α-(3-trifluoromethylphenoxy)-4-chlorobenzyl]-2-oxazoline; 2-[α-(3-trifluoromethylphenoxy)-4-chlorobenzyl]oxazole and 5-[α-(3trifluoromethylphenoxy)-4-chlorobenzyl]tetrazole. The following equation illustrates this process:

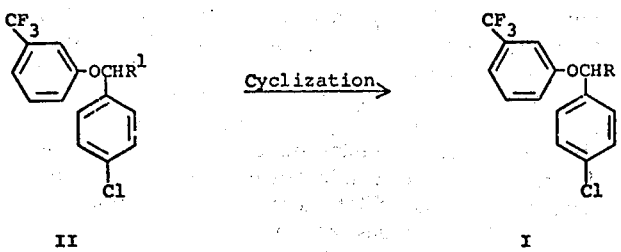

wherein R is as defined above and $R^1$ is hydroxy lower alkyl aminocarbonyl such as hydroxyethylaminocarbonyl and the like; dichloro lower alkyl aminocarbonyl such as dichloroethylaminocarbonyl and the like or iminoazidomethyl.

The first of the above-mentioned procedures comprises treating an N-(2-hydroxyethyl) (3-trifluoromethylphenoxy) (4-chlorophenyl)acetamide (IIa, infra) with a cyclizing agent, for example, thionyl chloride, phosphorus oxychloride and the like. The reaction is conducted employing as a solvent an excess of the cyclizing agent. The reaction is conducted at a temperature in the range of from about 0° to about 50°C. for a period of time of from about 15 hours to about 25 hours. The following equation illustrates this method of preparation:

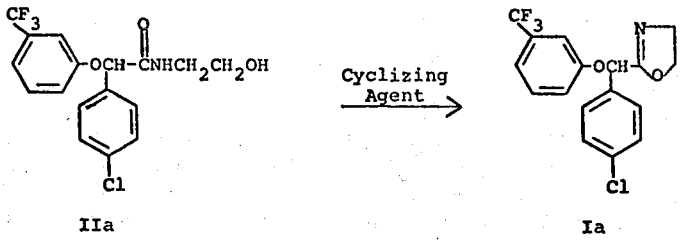

The second of the above-mentioned procedures comprises treating an N-(β,β-dichloroethyl)(3-trifluoromethylphenoxy) (4-chlorophenyl)acetamide (IIb, infra) with a cyclizing agent, preferably a base, for example, an alkali metal alkoxide such as sodium methoxide, sodium ethoxide, potassium methoxide, potassium tert-butoxide and the like in the presence of an alkanol solvent. Preferably the alkanol will correspond to the alkoxide portion of the alkali metal alkoxide. It has been found convenient to conduct the reaction at the reflux temperature of the particular solvent employed. The reaction is generally completed in about 30 minutes. The following equation illustrates this process:

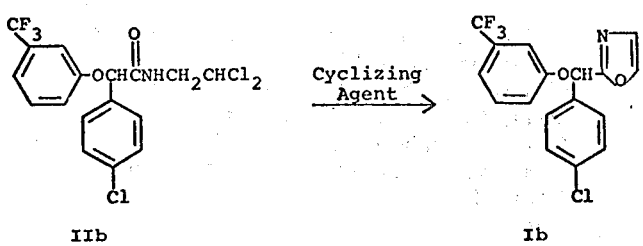

IIb  →  Cyclizing Agent  →  Ib

The third of the above-mentioned procedures comprises treating (3-trifluoromethylphenoxy)(4-chlorophenyl)acetonitrile (III, infra) with an azide, preferably an inorganic azide such as sodium azide, lithium azide, ammonium azide, aluminum azide and the like and preferably in the presence of a catalyst such as ammonium chloride, lithium chloride and the like. Any solvent which is inert or substantially inert to the reactants may be employed, for example, dimethylsulfoxide, hexamethylphosphoramide, dimethylformamide, tetrahydrofuran and the like. The intermediate iminoazide (IIc, infra) cyclizes under these reaction conditions. The reaction may be conducted at a temperature in the range of from about 50° to about 100°C. The following equation illustrates this reaction:

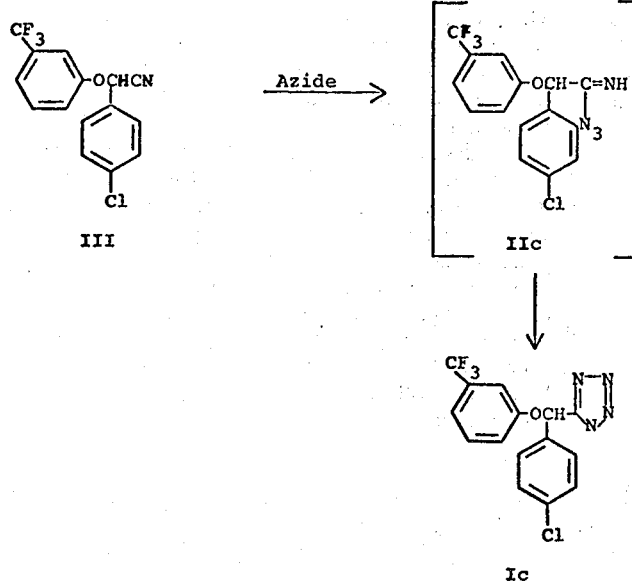

III  →  Azide  →  IIc  →  Ic

The N-($\beta$, $\beta$-dichloroethyl) (3-trifluoromethylphenoxy)(4-chlorophenyl)acetamide (IIb, supra) employed above is prepared by treating (3-trifluoromethylphenoxy) (4-chlorophenyl)acetyl chloride with $\beta,\beta$-dichloroethylamine at a temperature in the range of from 0°–10°C. for a period of time of from about 1 hour to about 2 hours. Any solvent which is inert or substantially inert to the reactants may be employed such as ether, chloroform, carbon tetrachloride, methylene chloride, tetrahydrofuran, benzene and the like.

The (3-trifluoromethylphenoxy) (4-chlorophenyl)acetonitrile (III) employed above is prepared by treating (3-trifluoromethylphenoxy) (4-chlorophenyl)acetamide with a dehydrating agent, for example, phosphorus oxychloride, phosphorus pentoxide and the like at a temperature in the range of from about −10° to about 25°C. in a suitable inert solvent, for example, hexamethylphosphoramide, dimethylformamide and the like. (An amine such as triethylamine is employed to react with any acid byproducts.) In lieu of the dehydrating agents mentioned above, there may also be employed lower alkanoic acid anhydrides, for example, acetic anhydride and the like. When the anhydrides are employed, the reaction is conveniently conducted at the reflux temperature of the particular anhydride employed.

Also included within the scope of this invention are the non-toxic, pharmaceutically acceptable salts. For example, when the heterocycle is a tetrazolyl radical the salts include metallic salts such as sodium, potassium, calcium and the like, the ammonium salt and substituted ammonium salts, for example, trialkylamines such as triethylamine, dibenzylamine and the like. When the heterocycle is an oxazolinyl or oxazolyl radical, the salts are the acid addition salts, for example, those derived from the inorganic acids such as hydrochloric acid and the like.

The examples which follow illustrate the [α-(3-trifluoromethylphenoxy)-4-chlorobenzyl]heterocycles of this invention and the methods by which they are prepared. However, the examples are illustrative only and it will be apparent to those having ordinary skill in the art that the instant products may be prepared in an analogous manner by variations of the methods disclosed in the examples.

EXAMPLE 1

2-[α-(3-Trifluoromethylphenoxy)-4-chlorobenzyl]-2-oxazoline Hydrochloride

N-(2-hydroxyethyl) (3-trifluoromethylphenoxy)(4-chlorophenyl)acetamide (30.5 g.) is treated with thionyl chloride (135 ml.) at room temperature. The solution is stirred at room temperature for 3 hours and allowed to stand at room temperature overnight. The excess thionyl chloride is removed under vacuum and the residue triturated with petroleum ether until it solidifies. The solid is collected and dissolved in hot methylcyclohexane (100 ml.). A dark oil precipitates on cooling and the methylcyclohexane is decanted. The oily precipitate is extracted four more times with methylcyclohexane (100 ml. portions) in the same way. The supernatent methylcyclohexane solutions are combined and concentrated in vacuo to remove the solvent. The residue is crystallized from isopropyl ether (50 ml.) to afford 20.1 g. of crude product, m.p. 87°–90°C. A second recrystallization from isopropyl ether (40 ml.) affords 15.2 g. of substantially pure 2-[α-(3-trifluoromethylphenoxy)-4-chlorobenzyl]-2-oxazoline hydrochloride, m.p. 90°–91.5°C. A sample recrystallized for analysis, m.p. 89.5°–91.5°C.

Elemental analysis for $C_{17}H_{13}ClF_3NO_2.HCl$: Calc: C, 52.06; H, 3.60; N, 3.57; Found: C, 52.30; H, 3.50; N, 3.56.

EXAMPLE 2

2-[α-(3-Trifluoromethylphenoxy)-4-chlorobenzyl]oxazole

Step A: N-(β,β-Dichloroethyl) (3-trifluoromethylphenoxy) (4-chlorophenyl)acetamide (3-Trifluoromethylphenoxy) (4-chlorophenyl)acetic acid (6.6 g., 0.02 mole) is placed in a 25 ml. 3-necked flask fitted with a condenser, stirrer and an addition of thionyl chloride (2.2 ml, 0.03 mole) over a 2-minute period at room temperature. The reaction mixture is refluxed for 5 hours and the solvent removed under vacuum to afford (3-trifluoromethylphenoxy) (4-chlorophenyl)acetyl chloride which is employed without purification.

β,β-Dichloroethylamine hydrochloride (3.66 g., 0.025 mole) is dissolved in a sodium hydroxide solution (15 ml., 2.5 N) and extracted with ether. The ether solution is dried over magnesium sulfate, filtered and then placed in a 100 ml. 3-necked flask. Triethylamine (3.4 ml., 0.025 mole) is then added and the solution is cooled in an ice bath. To this solution is added (3-trifluoromethylphenoxy) (4-chlorophenyl)acetyl chloride in ether (10 ml.) over a 15-minute period. The reaction mixture is stirred at 0°C. for 70 minutes. The reaction mixture is filtered and the ether filtrate is washed successively with hydrochloric acid (2 × 12 ml., 1 N), a sodium hydroxide solution (2 × 12 ml., 1 N) and then with water until neutral. The ether solution is dried over magnesium sulfate, filtered and the ether removed to afford 7.97 g. of crude N-(β,β-dichloroethyl) (3-trifluoromethylphenoxy) (4-chlorophenyl)acetamide. Recrystallization from n-hexane affords substantially pure product, m.p. 96°–98°C.

Elemental analysis for $C_{17}H_{13}Cl_3F_3NO_2$: Calc: C, 47.85; H, 3.07; N, 3.28; Found: C, 47.82; H, 2.94; N, 3.35.

Step B: 2-[α-(3-Trifluoromethylphenoxy)-4Chlorobenzyl]oxazole

Sodium (0.595 g., 0.026 mole) is dissolved in absolute ethanol (20 ml.). N-(β,β-dichloroethyl) (3-trifluoromethylphenoxy) (4-chlorophenyl)acetamide (4.69 g., 0.011 mole) is then added and the solution refluxed for 20 minutes. A precipitate forms and the solution becomes dark orange and then brown. The reaction mixture is cooled in an ice bath and then diluted with 50 ml. of water. The solution is extracted with 50 ml. of ether and then with 2 × 25 ml. of ether. The ether extracts are combined and washed successively with a sodium hydroxide solution (2 × 25 ml., 1 N), hydrochloric acid (2 × 25 ml., 1 N) and then with water until neutral. The ether solution is then washed with a saturated sodium chloride solution (25 ml.), treated with charcoal and then filtered to remove the charcoal. The ether solution is then dried over anhydrous magnesium sulfate, filtered and the ether removed under vacuum to afford 3.24 g. of an orange oil. The orange oil is dissolved in chloroform and chromatographed on a silica gel column employing as the eluant a mixture of chloroform and ethyl acetate (20:1). One ml. portions are collected and analyzed by thin layer chromatography and IR. The first 32 ml. collected contain no product. The next 18 ml. contain a mixture of starting material and final product. The next 53 ml. contain 2.03 g. of product obtained by evaporation of the solvent. Recrystallization from n-hexane affords 2-[α-(3-trifluoromethylphenoxy) 4-chlorobenzyl]oxazole, m.p. 66°–67°C.

Elemental analysis for $C_{17}H_{11}ClF_3NO_2$: Calc: C, 57.71; H, 3.14; N, 3.96; Found: C, 57.75; H, 3.50; N, 4.00.

EXAMPLE 3

5-[α-(3-Trifluoromethylphenoxy)-4-chlorobenzyl]tetrazole

Step A: (3-Trifluoromethylphenoxy) (4-chlorophenyl)acetonitrile (3-Trifluoromethylphenoxy) (4-chlorophenyl)acetamide, (33.0 g., 0.1 mole) is dissolved in 250 ml. of phosphorus oxychloride and triethylamine (22.2 g.) is added over a 45-minute period with stirring while maintaining the temperature of the solution at 0°–2°C. Over a period of an hour the temperature is allowed to rise to 25°C. and then the solution is heated under reflux for 30 minutes. The solution is concentrated in vacuo (about 200 mm.) to remove volatile products and excess phosphorus oxychloride. Toluene (150 ml.) and ice water (250 ml.) are added to the residue. The toluene layer is separated and the aqueous phase is extracted with 3 × 75 ml. of toluene. The toluene solutions are combined and extracted with 0.5 N sodium hydroxide and then with water. The toluene solvent is removed in vacuo and the residue is distilled in vacuo (0.3 mm.). (3-Trifluoromethylphenoxy) (4-chlorophenyl)acetonitrile (27.6 g.) boiling at 144°–145°C. is obtained.

Elemental analysis for $C_{15}H_9ClF_3NO$: Calc.: C, 57.80; H, 2.91; N, 4.49; Found: C, 58.02; H, 3.02; N, 4.37.

Step B: 5-[α-(3-Trifluoromethylphenoxyl)-4-chlorobenzyl]tetrazole

A mixture of (3-trifluoromethylphenoxy) (4-chlorophenyl)acetonitrile (10.68 g.), sodium azide (2.40 g.), ammonium chloride (1.98 g.) and hexamethylphosphoramide (85 ml.) is stirred at 60°–63°C. overnight (19 hours). The reaction mixture is cooled, poured into one liter of ice water containing 25 ml. of concentrated hydrochloric acid and this solution is extracted with 5 × 100 ml. of ether. The ether extracts are combined, extracted with water and dried over sodium sulfate. The ether solution is filtered, the ether is evaporated in vacuo and the residue is crystallized by trituration with methylcyclohexane. Recrystallization from a butyl chloride and methylcyclohexane mixture (about 1 to 1) affords 5-[α-(3-trifluoromethylphenoxy)-4-chlorobenzyl]tetrazole, m.p. 124.5°–126.5°C.

Elemental analysis for $C_{15}H_{10}ClF_3N_4O$: Calc.: C, 50.79; H, 2.84; N, 15.80; Found: C, 51.01; H, 2.88; N, 16.00.

The products of the invention can be administered in a wide variety of therapeutic dosages in conventional vehicles as, for example, by oral administration in the form of a capsule or tablet as well as by intravenous injection or oral solutions or suspensions. Also, the dosage of the products may be varied over a wide range as, for example, in the form of capsules or scored tablets containing 5, 10, 20, 25, 50, 100, 150, 250 and 500 milligrams, i.e., from 5 to about 500 milligrams, of the active ingredient for the symptomatic adjustment of the dosage to the patient to be treated. These dosages are well below the toxic or lethal dose of the products.

A suitable unit dosage form of the products of this invention can be prepared by mixing 50 mg. of [α-(3-trifluoromethylphenoxy)-4-chlorobenzyl]heterocycles or a suitable salt thereof, with 144 mg. of lactose and 6 mg. of magnesium stearate and placing the 200 mg. mixture into a No. 3 gelatin capsule. Similarly, by employing more of the active ingredient and less lactose, other dosage forms can be put up in No. 3 gelatin capsules and, should it be necessary to mix more than 200 mg. of ingredients together, larger capsules may be employed. Compressed tablets, pills or other desired unit dosages can be prepared to incorporate the compounds of this invention by conventional methods and, if desired, can be made as elixirs or as injectable solutions by methods well known to pharmacists.

It is also within the scope of this invention to combine two or more of the compounds of this invention in a unit dosage form or to combine one or more of the compounds with other known hypocholesterolemics and hypolipemics or with other desired therapeutic and/or nutritive agents in dosage unit form.

The following example is included to illustrate the preparation of a representative dosage form:

EXAMPLE 4

Dry-filled capsules containing 50 mg. of active ingredient per capsule

|  | Per Capsule |
|---|---|
| 5-[α-(3-Trifluoromethylphenoxy)-4-chlorobenzyl]-tetrazole | 50 mg. |
| Lactose | 144 mg. |
| Magnesium stearate | 6 mg. |
| Capsule Size No. 3 | 200 mg. |

The 5-[α-(3-trifluoromethylphenoxy)-4-chlorobenzyl]tetrazole is reduced to a No. 60 powder and then lactose and magnesium stearate are passed through a No. 60 bolting cloth onto the powder and the combined ingredients admixed for 10 minutes and then filled into No. 3 dry gelatin capsules.

Similar dry-filled capsules can be prepared by replacing the active ingredient of the above example by any of the other novel compounds of this invention.

It will be apparent from the foregoing description that the [α-(3-trifluoromethylphenoxy)-4-chlorobenzyl]heterocycles of this invention and their salt derivatives constitute a valuable class of compounds which have not been prepared before. One skilled in the art will also appreciate that the processes disclosed in the above examples are merely illustrative and are capable of a wide variation and modification without departing from the spirit of this invention.

What is claimed is:

1. A compound of the formula:

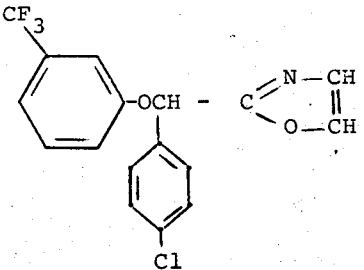

and non-toxic, pharmaceutically acceptable salts thereof.

* * * * *

UNITED STATES PATENT OFFICE
CERTIFICATE OF CORRECTION

PATENT NO. : 3,953,465
DATED : April 27, 1976
INVENTOR(S) : WILLIAM A. BOLHOFER

It is certified that error appears in the above-identified patent and that said Letters Patent are hereby corrected as shown below:

Title pg., left col., first line delete "2-[α-(3-trifluoromethylphenoxyl)-" and insert --- 2-[α-(3-trifluoromethylphenoxy)- ---. (Deleting the "l" in phenoxy).

Col. 1, line 1, delete "trifluoromethylphenoxyl)" and insert --- trifluoromethylphenoxy) ---. (Deleting the "l" in phenoxy).

Col. 5, line 30, after the word, "addition" insert --- funnel. Chloroform (10 ml.) is added followed by the addition ---. (Line was omitted).

Signed and Sealed this

Third Day of August 1976

[SEAL]

Attest:

RUTH C. MASON
Attesting Officer

C. MARSHALL DANN
Commissioner of Patents and Trademarks